(12) United States Patent
Fluharty et al.

(10) Patent No.: US 6,242,191 B1
(45) Date of Patent: Jun. 5, 2001

(54) METHODS FOR ASSESSING THE BEEF CHARACTERISTICS OF LIVE CATTLE

(75) Inventors: Francis Fluharty; Daral J. Jackwood, both of Wooster, OH (US)

(73) Assignee: The Ohio State University Research Foundation, Columbus, OH (US)

(*) Notice: Subject to any disclaimer, the term of this patent is extended or adjusted under 35 U.S.C. 154(b) by 0 days.

(21) Appl. No.: 09/475,838

(22) Filed: Dec. 30, 1999

(51) Int. Cl.[7] .............................. C12Q 1/68; C12P 19/34; C07H 21/04
(52) U.S. Cl. ............................. 435/6; 435/91.2; 435/810; 536/23.1; 536/24.31; 536/24.33
(58) Field of Search ............................... 435/6, 91.2, 810; 536/23.1, 24.31, 24.33

(56) References Cited

U.S. PATENT DOCUMENTS 5,126,239 * 6/1992 Livak et al. ............................... 435/6

OTHER PUBLICATIONS

Lee et al. RDA Journal of Agricultural Science. 36:222–226, 1994.*
"Effect of pH, Temperature, and Inhibitors and Autolysis and Catalytic Activity of Bovine Skeletal Muscle μ–Calpain" by Koohmaraie, *J. Anim. Sci.*, 1992, 70:3071–7380.
"Optimisation of Tenderisation, Ageing and Tenderness" by Dransfield, *Meat Science*, 36 (1994) 106–121.
"Effects of Animal Age, Marbling Score, Calpastatin Activity, Subprimal, Cut, Calcium Injection, and Degree of Doneness on the Palatability of Steaks from Limousine Steers" by Wulf, et al., *J. Anim. Sci.*, 1996, 74:569–576.

(List continued on next page.)

*Primary Examiner*—Carla J. Myers
(74) *Attorney, Agent, or Firm*—Calfee, Halter & Griswold LLP

(57) ABSTRACT

Methods for identifying cattle and beef carcasses that have markers of beef tenderness are provided The methods comprise extracting DNA from a sample obtained from a bovine animal or beef carcass, amplifying the extracted DNA using a primer referred to hereinafter as the "CSTN" primer and low stringency polymerase chain reaction (PCR) conditions to provide a pool of PCR products, and then assaying the pool for the presence or absence of a PCR product of approximately 350 base pairs, a PCR product of approximately 625 base pairs, a PCR product of approximately 675 base pairs, a PCR product of approximately 1450 base pairs, or combinations thereof. The CSTN primer is a single stranded oligonucleotide of from 8 to 12 nucleotides and having the sequence 5' CGGGCAGG-3', SEQ ID NO:1. Methods for identifying cattle and carcasses that have markers of beef marbling are also provided. The method comprise extracting DNA from a tissue sample from a bovine animal or beef carcass, amplifying the extracted DNA using a primer referred to hereinafter as the "CPN" primer and low stringency PCR conditions to provide a pool of PCR products, and then assaying the pool for the presence or absence of a PCR product of approximately 175 base pairs, or a PCR product of approximately 600 base pairs, or both PCR products. The CPN primer is a single stranded oligonucleotide comprising from 9 to 12 nucleotides and having the sequence 5'GCGCGAACG-3', SEQ ID NO:3.

19 Claims, 2 Drawing Sheets

RAPD band generated using the CSTN primer. First and last lanes are 100 bp size markers. Lanes inbetween the size markers are samples from different cattle. The bands that have a statistical relationship with shear force data are marked (350, 625, 675, and 1450).

OTHER PUBLICATIONS

"Heritabilities and Phenotypic and Genetic Correlations for Bovine Postrigor Calpastatin Activity, Intramuscular Fat Conent, Warner–Bratzler Shear Force, Retail Product Yield, and Growth Rate" by Shackelford, et al., *J. Anim. Sci.*, 1994, 72:857–863.

"Effect of pH and Ionic Strength on Bovine m–Calpain and Calpastatin Activity" by Kendall, et al., *J. Anim. Sci.*, 1993, 71:96–104.

"Meat Tenderness and the Calpain Proteolytic System in Longissimus Muscle of Young Bulls and Steers" by Morgan, et al., *J. Anim. Sci.*, 1993, 71:1471–1476.

"Rapid Communication: A Polymorphic Microsattelite in the Promoter Region of the Bovine Calpastatin Gene" by Nonneman, et al., *J. Animl Sci.*, 1999, 77:3114–3115.

"Rapid Communication: A TaqI Restriction Fragment Length Polymorphism in the Bovine Calpastatin Gene" by Cockett, et al., *J. Animl Sci.*, 1995, 73:3790.

"Modeling Post–Mortem Tenderisation–IV: Role of Calpains and Calpastatin in Conditioning" by Dransfield, *Meat Science*, 34 (1993) 217–234.

"Relationship of Restriction Fragment Length Polymorphisms (RFLP) at the Bovine Calpastatin Locus to Calpastatin Activity and Meat Tenderness" by Lonergan, et al., *J. Anim. Sci.*, 1995, 73:3608–3612.

"Application of Ultrasound for Feeding and Finishing Animals: A Review" by Houghton, et al., *J. Anim. Sci.*, 1992, 70:930–941.

"Principles of Ultrasound and Measurement of Intramuscular Fat" by Whittaker, et al., *J. Anim. Sci.*, 1992, 70:942–952.

"The Role of Instrument Grading in a Beef Value–Based Marketing System", by Cross, et al., *J. Anim. Sci.*, 1992, 70:984–989.

"Estimating Marbling Score in Live Cattle from Ultrasound Images Using Pattern Recognition and Neural Network Procedures" by Brethour, *J. Anim. Sci.*, 1994, 72:1425–1432.

"Genetic Parameter Estimates of Live Animal Ultrasonic Measures of Retail Yield Indicators in Yearling Breeding Cattle" by Shepard, et al., *J. Anim. Sci.*, 1996, 74:761–768.

"Use of Real–Time Ultrasonund to Evaluate Live Animal Carcass Traits in Young Performance–Tested Beef Bull" by Bergen, *J. Anim. Sci.*, 1997, 75:2300–2307.

"Comparison of Four Real–Time Ultrasound Systems that Predict Intramuscular Fat in Beef Cattle" by Herring, et al., *J. Anim. Sci.*, 1998, 76:364–370.

"Repeatability of Ultrasound–Predicted Percentage of Instramuscular Far in Feedlot Cattle" by Hassen, et al. *J. Anim. Sci.*, 1999, 77:1335–1340.

"Predicating Carcass Composition of Beef Cattle Using Ultrasound Technology" by Griffin, et al., *J. Anim. Sci.*, 1999, 77:889–892.

"Evaluation of Carcass, Live, and Real–Time Ultrasound Measures in Feedlot Cattle: II. Effects of Different Age End Points on the Accuracy of Predicting the Percentage of Retail Product, Retail Product Weight, and Hot Carcass Weight" by Hassen, et al., *J. Anim. Sci.*, 1999, 77:283–290.

\* cited by examiner

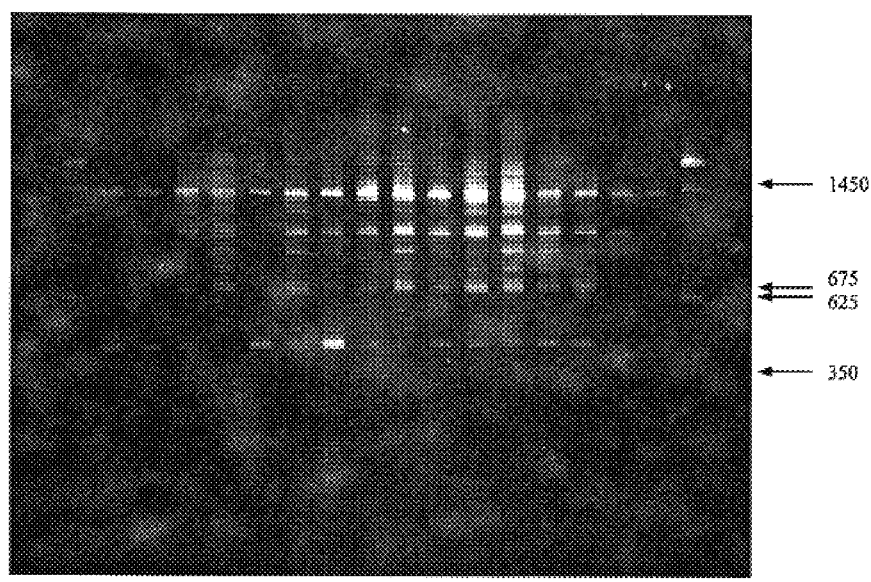
Figure 1. RAPD band generated using the CSTN primer. First and last lanes are 100 bp size markers. Lanes inbetween the size markers are samples from different cattle. The bands that have a statistical relationship with shear force data are marked (350, 625, 675, and 1450).

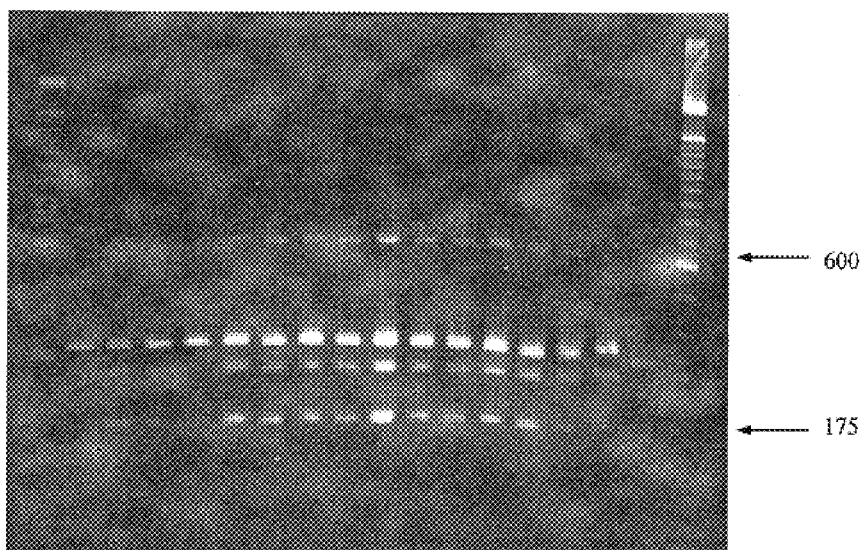
Figure 2. RAPD bands generated using the CPN primer. First and last lanes are 100 bp size markers. Lanes inbetween the size markers are samples from different cattle. The bands that have a statistical relationship with quality grade data are marked (600 and 175).

SEQUENCE LISTING

<160> NUMBER OF SEQ ID NOS: 4

<210> SEQ ID NO: 1
<211> LENGTH: 8
<212> TYPE: DNA
<213> ORGANISM: CSTN primer

<400> SEQUENCE: 1 cgggcagg                                                        8

<210> SEQ ID NO: 2
<211> LENGTH: 10
<212> TYPE: DNA
<213> ORGANISM: CSTN primer

<400> SEQUENCE: 2
cgggcaggat                                                     10

<210> SEQ ID NO: 3
<211> LENGTH: 9
<212> TYPE: DNA
<213> ORGANISM: CPN primer

<400> SEQUENCE: 3 gcgcgaacg                                                       9

<210> SEQ ID NO: 4
<211> LENGTH: 10
<212> TYPE: DNA
<213> ORGANISM: CPN primer

<400> SEQUENCE: 4
gcgcgaacga                                                     10

METHODS FOR ASSESSING THE BEEF CHARACTERISTICS OF LIVE CATTLE

BACKGROUND

Under the current standards established by the United States Department of Agriculture (USDA), beef from bulls, steers, and heifers is classified into eight different quality grades. Beginning with the highest and continuing to the lowest, the eight quality grades are prime, choice, select, standard, commercial, utility, cutter and canner. The characteristics which are used to classify beef include color, texture, firmness, and marbling, a term which is used to describe the relative amount of intramuscular fat of the beef. Well-marbled beef from steers and heifers, i.e., beef that contains substantial amounts of intramuscular fat relative to muscle, tends to be classified as prime or choice; whereas, beef that is not marbled tends to be classified as select. Beef that is classified as prime or choice, typically, is sold at higher prices than beef that is classified into lower quality grades.

Classification of beef into different quality grades is a subjective process which occurs at the packing facility and involves visual inspection of a region between the 12th and 13th rib of a beef carcass by a certified USDA grader. The grader relies on pictures and other objective aids to make his determinations as to color, texture, firmness, and marbling. Unfortunately, the visual appraisal by the grader is costly, labor intensive, and time-consuming. Moreover, the visual appraisal of a beef carcass cannot occur until the animals are harvested.

Currently there are no methods for identifying live cattle that have or that lack the genetic potential to produce beef that is well-marbled. Such information could be used by the cattle producer to channel calves into particular feeding regimens and to meet the requirements of specific marketing programs. Such information could also be used to identify cattle that are good candidates for breeding. Thus, it is desirable to have a method which can be used to assess the beef marbling potential of live cattle, particularly young cattle.

Another characteristic of beef that is desired by consumers is tenderness. Currently there are no procedures for identifying live animals whose beef, if cooked properly, would be tender Currently, there are two procedures which are used by researchers to assess the tenderness of beef after it has been cooked. The first involves a subjective analysis by a panel of trained testers. The second is the Warner-Bratzler shear force procedure which involves an instrumental measurement of the force required to shear steaks, chops, and ground patties of cooked beef. Both methods are costly and time-consuming and, thus, are not practical on a large scale. Consequently, neither procedure is used at a packing facility. Accordingly, it is desirable to have new methods which can be used to identify carcasses and live cattle that have the potential to provide beef that, if cooked properly, will be tender.

SUMMARY OF THE INVENTION

The present invention provides new methods for identifying cattle and beef carcasses that have markers of beef tenderness. The method comprises extracting DNA from a sample obtained from a bovine animal or beef carcass, amplifying the extracted DNA using a primer referred to hereinafter as the "CSTN" primer and low stringency polymerase chain reaction (PCR) conditions to provide a pool of PCR products, and then assaying the pool for the presence or absence of a PCR product of approximately 350 base pairs, a PCR product of approximately 625 base pairs, a PCR product of approximately 675 base pairs, a PCR product of approximately 1450 base pairs, or combinations thereof. Such PCR products are collectively referred to hereinafter as "markers of beef tenderness". The CSTN primer is a single stranded oligonucleotide of from 8 to 12 nucleotides and having the sequence 5'CGGGCAGG-3', SEQ ID NO:1. In a preferred embodiment, the CSTN primer has the sequence 5'-CGGGCAGGAT-3', SEQ ID NO:2. In accordance with the present method it has been determined that beef obtained from cattle or carcasses whose DNA generates at least one of the markers of tenderness is more tender, as assessed by the Warner-Bratzler shear force procedure, than cattle whose DNA does not generate any of these markers of beef tenderness. It has also been determined that beef obtained from cattle whose DNA generates any two of these four markers of tenderness is more tender than beef obtained from cattle whose DNA generates a single marker of tenderness. It has also been determined that cattle whose DNA generates four markers of beef tenderness provide beef that is more tender that cattle whose DNA generates less than four markers of beef tenderness. Thus, the present method is useful for identifying cattle and carcasses whose beef, if cooked properly, will be tender.

The present invention also provides new methods for identifying cattle and carcasses that have markers of beef marbling. The method comprises extracting DNA from a tissue sample from a bovine animal or beef carcass, amplifying the extracted DNA using a primer referred to hereinafter as the "CPN" primer and low stringency PCR conditions to provide a pool of PCR products, and then assaying the pool for the presence or absence of a PCR product of approximately 175 base pairs, referred to hereinafter as the "first marker of beef marbling", or a PCR product of approximately 600 base pairs, referred to hereinafter as the "second marker of beef marbling". Preferably, the method comprises assaying for the presence of both the first marker and the second marker of beef marbling. The CPN primer is a single stranded oligonucleotide comprising from 9 to 12 nucleotides and having the sequence 5'GCGCGAACG-3', SEQ ID NO:3. In a preferred embodiment, the CPN primer has the sequence 5'-GCGCGAACGA-3', SEQ ID NO:4. In accordance with the present method, it has been determined that beef obtained from cattle whose DNA generates the first marker of marbling has a higher degree of marbling than beef that has been obtained from cattle whose DNA does not generate the first marker of marbling. Cattle whose DNA generates the second marker of marbling in addition to the first marker of marbling provide beef that has an even higher degree of marbling than beef obtained from cattle whose DNA generates only the first marker of marbling.

The present invention also relates to CSTN primers and CPN primers. The present invention also relates to a kit comprising a first container containing a CSTN primer and a second container containing a CPN primer.

BRIEF DESCRIPTION OF THE FIGURES

FIG. 1 shows the number and size of the PCR products produced when blood samples from 16 different cattle were tested using the present method and a CSTN primer having the sequence of SEQ ID.NO:2.

FIG. 2 shows the number and size of the PCR products produced when blood samples from 16 different cattle were tested using the present method and a CPN primer having the sequence of SEQ ID NO:4.

DETAILED DESCRIPTION OF THE INVENTION

The present invention provides new methods for identifying cattle and beef carcasses whose DNA contain markers of marbling. The method comprises extracting DNA from a tissue sample from a bovine animal or a beef carcass, amplifying the extracted DNA using a CPN primer and low stringency PCR conditions to provide a pool of PCR products, and then assessing the size of the PCR products in the pool to detect the presence or absence of a PCR product of approximately 175 base pairs, or a PCR product of approximately 600 base pairs, or both PCR products. As used herein the term approximately means that size of the PCR products comprised of less than 1000 base pairs varies no more than plus or minus 5% from the designated number of base pairs and that the size of the PCR products comprised of 1000 base pairs or greater varies no more than plus or minus 10% from the designated number of base pairs. The present invention also provides a method for identifying cattle and beef carcasses whose DNA contain markers of beef tenderness. The method comprises extracting DNA from a sample obtained from a bovine animal or beef carcass, amplifying the extracted DNA using a CSTN primer and low stringency PCR conditions to provide a pool of PCR products, and then assessing the size of the PCR products in the pool to detect the presence or absence of a PCR product of approximately 350 base pairs, or a PCR product of approximately 625 base pairs, or a PCR product of approximately 675 base pairs, or a PCR product of approximately 1450 base pairs, or a combination of two or more of such products.

SAMPLE

The sample is a tissue sample or bodily fluid containing DNA. For animals that have not been harvested, the preferred sample is blood or semen For a beef carcass, the preferred sample is muscle tissue which has been sliced from the carcass.

PRIMERS

The CPN primer is a single stranded oligonucleotide of from 9 to 12 nucleotides and comprising the sequence 5'GCGCGAACG-3', SEQ ID NO:3. In a preferred embodiment, the CPN primer is a 10 nucleotide oligomer which has the sequence 5'-GCGCGAACGA-3', SEQ ID NO:4. CPN primers which are longer than 10 nucleotides in length have one or two additional nucleotides attached to the 3' end of SEQ ID NO:4. The additional nucleotides are selected from the group consisting of adenylic acid, guanylic acid, and combinations thereof. It has been determined that approximately 12 PCR products having sizes ranging from about 175 base pairs to about 1500 base pairs are produced when samples are tested using a CPN primer having the sequence of SEQ ID NO:4 and low stringency PCR conditions.

The CSTN primer is a single stranded oligonucleotide of from 8 to 12 nucleotides and comprising the sequence 5'CGGGCAGG-3', SEQ ID NO:1. In a preferred embodiment, the CSTN primer is a 10 nucleotide oligomer which has the sequence 5'-CGGGCAGGAT-3', SEQ ID NO:2. CSTN primers which are longer than 10 nucleotides in length have one or two additional nucleotides attached to the 3' end of SEQ ID NO:2. The additional nucleotides are selected from the group consisting of adenylic acid, guanylic acid, and combinations thereof. It has been determined that approximately 27 PCR products ranging in size from about 350 base pairs to about 1500 base pairs are produced when DNA samples are tested using a CSTN primer having the sequence of SEQ ID NO:2 and low stringency PCR conditions.

CPN primers and CSTN primers are made using synthetic methods.

METHODS

DNA is extracted by standard methods. For example, DNA may be extracted from bodily fluids, such as blood or semen, using commercially available PCR filters such as, for example, the Isocode filters which are available from Schleicher and Schuell, New Hampshire. Methods of extracting DNA from tissue samples, such as muscle tissues, are described in Maniatis, T., J. Sambrook, and E. F. Fritsch. 1989. Molecular Cloning: a Laboratory manual, 2nd ed. Cold Spring Harbor Laboratory Press, Cold Spring Harbor N.Y., which is specifically incorporated herein by reference.

The DNA is then amplified with the CSTN or CPN primer and low stringency PCR conditions. As used herein "low stringency PCR conditions" refers to conditions equivalent to or comparable to denaturation for 1 minute at 95° C. in a solution comprising 10 mM Tris-HCl (pH 8.3), 50 mM KCl and 2.5 mM $MgCl_2$, followed by annealing in the same solution at about 37° C. for 1.5 minutes. As recognized in the art, suitable stringency conditions can be attained by varying a number of factors such as the length and nature, i.e., DNA or RNA, of the primer; the length and nature of the target sequence; the concentration of the salts and other components of the PCR solution; the temperature and time of each step, e.g., denaturation, annealing, and elongation. All of these factors may be varied to generate conditions of stringency which are equivalent to the conditions listed above. Changes in stringency are accomplished primarily through the manipulation of annealing temperature and time.

Thereafter, the size of the PCR products produced during PCR are determined. Preferably the size of the PCR products is determined using gel electrophoresis and a plurality of DNA standards of varying sizes. The PCR products and DNA standards that are present on the gel are visualized using standard techniques, such as ethidium bromide staining.

Advantageously, the present methods can be used to identify live animals that have the potential to provide beef that is tender and well-marbled long before harvesting. Accordingly, the present methods enable the cattle producer to channel the cattle into appropriate feeding regimens. Moreover, because the present methods are based on the genetic make-up of the animal, the present methods are also useful for identifying heifers and bulls that have the genetic potential to pass these traits onto their progeny.

Furthermore the present methods for identifying carcasses with these desirable traits can employ a scraping or slice of tissue from the surface of the carcass. Such sampling technique is not invasive and, thus, is not likely to lead to contamination of the carcass. Accordingly, the present method for identifying carcasses having markers of tenderness and marbling can be used at the packing facility without running afoul of USDA standards.

EXAMPLES

Extraction of Cattle DNA

Whole blood from cattle was collected using a needle and syringe. Three drops of blood were placed onto Isocode filters (Schleicher and Schuell, New Hampshire) specially designed for PCR DNA samples. The filter was air-dried and stored at room temperature. A 1.0 mm×1.0 mm section of the Isocode filter containing dried whole cattle blood was placed in a 1.5 ml eppendorf tube containing 0.5 ml sterile water and mixed for 5 seconds. The filter section was removed, placed in a second 1.5 ml eppendorf tube containing 0.5 ml sterile water and mixed for 5 seconds. This washing procedure was repeated one more time.

After the third rinse, the filter section was placed in an 0.5 ml eppendorf tube containing 0.2 ml sterile water. The tube and contents were heated for 30 minutes at 95° C. After the 30 minute incubation, the filter section was removed and a 10 $\mu$l volume of the aqueous solution containing cattle DNA was used in a random amplified polymorphic DNA (RAPD) procedure.

RAPD Procedure.

The RAPD procedure was conducted using a kit from Perkin Elmer Cetus of Norwalk, Conn. The assay was conducted in a Perkin Elmer thermal cycler. The reactions were initially incubated at 95° C. for 1 minute, followed by 40 cycles of denaturation at 95° C. for 1 minute, annealing at 37° C. for 1 minute 30 seconds, and elongation at 72° C. for 3 minutes Finally, the reactions were incubated at 72° C. for 7 minutes.

The reactions were conducted using the PCR kit as recommended by Perkin Elmer Cetus. Each reaction contained 10 µl cattle DNA sample, 10 µl 10X PCR buffer II, 200 µM each of dATP, dCTP, dGTP, dTTP, 2.5 mM MgCl$_2$, and 0.2 µM of the CSTN or CPN primer. The total reaction volume was increased to 100 µl using sterile water and prior. Prior to conducting the PCR incubations, AmpliTaq DNA polymerase (2.5 Units) was added to each reaction.

RAPD Analysis

The PCR products were visualized using standard techniques of agarose gel electrophoresis. A 2% agarose gel (FMC BioProducts, Rockland, Md.) was prepared in TNE buffer (10 mM Tris-HCL[pH 8.0], 100 ; mM NaCl, 1 mM ethylenediaminetetraacetic acid). The PCR products were separated using electrophoresis and then visualized using ethidium bromide staining. Sizes of the RAPD bands were determined by comparison to a 100 bp DNA ladder control from Promega, Corp. Madison, Wis.

Example 1

A CSTN primer having the sequence 5'-CGGGCAGGAT-3', SEQ ID NO:2, was used in the above described RAPD procedure to detect the presence or absence of the four markers of tenderness in DNA obtained from 90 animals.

For comparison, the tenderness of the beef obtained from the carcass of each test animal was assessed using the Warner-Bratzler shear force procedure: Specifically, the 9–10–11th rib section was removed from the right side of each carcass 48 hours post-mortem. The 12th rib section was removed, vacuum packaged and frozen until analysis for shear force according to the procedures described in the American Meat Science Association: Research Guidelines for Cookery, Sensory Evaluation, and Instrumental Tenderness Measurements of Fresh Meat. (1995) Am. Meat Sci. Assoc., Chicago, Ill. On the day of analysis, the 12th rib section was sawed into a steak 2.54 cm thick. Steaks were cooked to an average internal temperature of 71.7° C., and five core samples were removed from each steak. The peak Warner-Bratzler shear force was determined for each of the five core samples. The numerical average (mean) of the five recorded peak shear forces was used as the shear force for a steak.

As shown below in Table 1, a total of twenty-nine bands ranging in size from 350 base pairs to 1500 base pairs were detected using this particular CSTN primer. To determine the statistical significance of each of the 29 bands, the mean shear force of the beef obtained from the animals whose DNA did not generate a particular band and the mean shear force of the beef obtained from the animals whose DNA did generate the band in question was compared using analysis of variance (ANOVA) as determined by the Statistical Analysis Software (SAS) program from the SAS Institute Inc., Cary, N.C. The results are shown below in Table 1.

TABLE I

Relationship between all RAPD bands (CSTN) with shear force (SF) means

| RAPD Band | No Band | | | Band Present | | |
|---|---|---|---|---|---|---|
| (BP) | N | Mean SF | SE | N | Mean SF | SE |
| 350[a] | 85 | 5.06 | .11 | 5 | 3.84 | .47 |
| 375 | 78 | 5.04 | .12 | 12 | 5.67 | .31 |
| 425 | 1 | 5.11 | 1.08 | 89 | 4.99 | .11 |
| 450 | 86 | 4.99 | .12 | 4 | 5.08 | .54 |
| 475 | 48 | 5.20 | .15 | 42 | 4.76 | .16 |
| 500 | 83 | 5.05 | .12 | 7 | 4.29 | .40 |
| 525 | 76 | 5.01 | .12 | 14 | 4.92 | .29 |
| 575 | 89 | 4.97 | .11 | 1 | 7.28 | 1.05 |
| 600 | 89 | 5.00 | .11 | 1 | 4.47 | 1.08 |
| 625[b] | 84 | 5.07 | .11 | 6 | 3.90 | .43 |
| 650 | 57 | 5.02 | .14 | 33 | 4.95 | .19 |
| 675[b] | 42 | 5.38 | .16 | 48 | 4.65 | .15 |
| 725 | 36 | 4.86 | .19 | 54 | 5.08 | .15 |
| 750 | 83 | 5.04 | .12 | 7 | 4.41 | .40 |
| 800 | 89 | 4.99 | .11 | 1 | 5.11 | 1.08 |
| 850 | 38 | 2.79 | .18 | 52 | 2.85 | .16 |
| 900 | 89 | 4.99 | .11 | 1 | 5.27 | 1.08 |
| 950 | 83 | 5.02 | .12 | 7 | 4.69 | .41 |
| 1000 | 24 | 5.21 | .22 | 66 | 4.91 | .13 |
| 1050 | 81 | 5.04 | .12 | 9 | 4.57 | .36 |
| 1100 | 85 | 5.03 | .12 | 5 | 4.38 | .48 |
| 1150 | 88 | 5.02 | .11 | 2 | 3.70 | .75 |
| 1200 | 77 | 4.96 | .12 | 13 | 5.19 | .30 |
| 1250 | 89 | 5.00 | .11 | 1 | 4.55 | 1.08 |
| 1350 | 81 | 4.96 | .12 | 9 | 5.32 | .36 |
| 1400 | 20 | 4.67 | .24 | 70 | 5.09 | .13 |
| 1450[b] | 79 | 5.11 | .12 | 11 | 4.19 | .31 |
| >1500 | 53 | 4.92 | .15 | 37 | 5.10 | .18 |

Bands in bold were statistically significant.
[a]Band effect (P < .05).
[b]Band effect (P < .01).

As shown in Table 1, four of the bands were statistically significant. As used herein the term "statistically significant band" means that the cooked beef obtained from an animal whose DNA generated the statistically significant band had a lower shear force than cooked beef obtained from all the animals whose DNA did not generate such band. In other words, the mean of the shear force of the cooked beef from animals whose DNA generated each of these four bands was statistically significantly less than the mean shear force of the cooked beef from animals whose DNA did not generate each of these bands. The four statistically significant bands, i.e., the four markers of tenderness, were comprised of 350 base pairs, 625 base pairs, 675 base pairs, and 1450 base pairs.

Table 2 shows the relationship between the statistically significant bands and the shear force of the cooked beef obtained from the animals whose DNA generated the statistically significant band.

TABLE 2

Relationship between statistically significant RAPD bands (CSTN) with shear force[a]

| None N | of the Bands Mean | SE | 4 675 band only N Mean | SE | Bands 675 Only N Mean | And 1450 SE |
|---|---|---|---|---|---|---|

TABLE 2-continued

Relationship between statistically significant RAPD bands (CSTN) with shear force[a]

| | | | | | | | | |
|---|---|---|---|---|---|---|---|---|
| Shear Force | 41 | 5.39[b] | .16 | 35 | 4.82[c] | .17 | 6 | 4.40[cd] | .41 |

| | Bands 625 | Only And | At 675 | All bands | | |
|---|---|---|---|---|---|---|
| | N | Mean | SE | N | Mean | SE |
| Shear Force | 2 | 4.45[bcd] | .72 | 4 | 3.62[d] | .51 |

[a]Only combinations with two or more observations.
[bcd]Means with different superscripts differ (P < .0033).

As shown in Table 2, the mean shear force of cooked beef obtained from animals whose DNA generated a band comprised of 675 base pairs was statistically significantly less than the mean shear force of cooked beef from animals whose DNA did not generate any of the 4 markers of tenderness. Similarly, animals whose DNA generated a 675 base pair band and a 1450 base pair band provided beef whose mean shear force was statistically significantly less than the mean shear force of beef obtained from animals whose DNA generated none of the markers of tenderness but was similar to the mean shear force of beef obtained from animals whose DNA generated only the 675 base pair band. The mean shear force of the beef obtained from animals whose DNA generated all four markers of tenderness was statistically significantly less than the mean shear force of the beef obtained from animals whose DNA did not generate any of the markers of tenderness, or whose DNA generated only the 675 base pair band, or whose DNA generated only the 675 base pair band and the 1450 base pair band, or whose DNA generated only the 625 base pair band and the 675 base pair band These results indicate that beef obtained from cattle whose DNA generates all four markers of tenderness is more tender than beef obtained from cattle whose DNA generates three markers of tenderness; that beef obtained from animals whose DNA generates three markers of tenderness is more tender than beef obtained from animals whose DNA generates two of the markers of tenderness; and that beef obtained from animals whose DNA generates the 675 base pair band and the 1450 base pair band is more tender than beef obtained from animals whose DNA generate only a single marker of tenderness.

Thus, the present method can be used to identify cattle and carcasses whose beef, if cooked properly, will be tender. Moreover, the present method can be used to classify cattle and beef carcasses into five categories of beef tenderness potential.

Example 2

A CPN primer having the sequence 5'-GCGCGAACGA-3', SEQ ID NO:4 was used in the above-described RAPD procedure to detect the presence or absence of markers of marbling in DNA obtained from blood samples taken from 191 animals that had been matched with respect to age and sex condition Following harvest, the quality grade, i.e., the degree of marbling in muscle obtained from the beef carcass of each animal was determined by a certified USDA grader according to the procedures set forth by the U.S.D.A. The animals exhibited five different degrees of marbling and were, thus, classified into 5 quality grades, including prime, choice[+], choice[°], choice[−], and select. A numerical value was assigned to each of the grades, with the highest grade, i.e. prime, being assigned a numerical value of "5" and the lowest grade i.e., select, being assigned a numerical value of "1. The relationship between each the 13 of the RAPD bands produced using this particular primer and the mean quality grade of the beef from the animals whose DNA did or did not generate the relevant band are shown below in Table 3.

TABLE 3

Relationship between all RAPD bands (CPN1) with quality grade (QG) mean[a]

| | No band | | | Band Present | | |
|---|---|---|---|---|---|---|
| RAPD band (BP) | N | QG mean | SE | N | QG mean | SE |
| 175[b] | 10 | 2.20 | .35 | 181 | 2.92 | .08 |
| 200 | 189 | 2.88 | .08 | 2 | 2.50 | .78 |
| 225 | 190 | 2.87 | .08 | 1 | 5.00 | 1.08 |
| 250 | 188 | 2.88 | .08 | 3 | 3.00 | .64 |
| 275 | 23 | 2.65 | .23 | 168 | 2.91 | .08 |
| 300 | 189 | 2.87 | .08 | 2 | 3.50 | .78 |
| 325 | 3 | 2.67 | .64 | 188 | 2.88 | .08 |
| 375 | 190 | 2.87 | .08 | 1 | 4.00 | 1.10 |
| 425 | 190 | 2.87 | .08 | 1 | 4.00 | 1.10 |
| 575 | 189 | 2.88 | .08 | 2 | 3.00 | .78 |
| 600[c] | 126 | 2.71 | .10 | 65 | 3.20 | .13 |
| 1250 | 187 | 2.88 | .08 | 4 | 2.75 | .55 |
| >1500 | 188 | 2.88 | .08 | 3 | 3.00 | .64 |

[a]1 = select, 2 = choice[−], 3 = choice[°], 4 = choice[+], 5 = prime.
Bands in bold were statistically significant.
[b]Band effect (P < .05).
[c]Band effect (P < .01).

As shown in Table 3, two of the PCR bands were statistically significant, as determined using ANOVA. These bands, which are referred to herein as markers of marbling, were comprised of about 175 base pairs and about 600 base pairs. Table 4 below shows the relationship between the markers of marbling and the quality grade of beef and the backfat depth of carcasses obtained from animals whose DNA did or did not generate these markers of marbling.

TABLE 4

Relationship between statistically significant RAPD bands (CPN1) with quality grade and backfat depth[a]

| | No n | 175 or Band Mean | 600 SE | N | 175 band Mean | Only SE | Both n | 175 and Band Mean | 600 SE |
|---|---|---|---|---|---|---|---|---|---|
| Quality grade[b] | 10 | 2.20[d] | .34 | 116 | 2.76[d] | .10 | 65 | 3.20[c] | .13 |
| Backfat depth, in | 10 | .55 | .05 | 116 | .54 | .02 | 65 | .60 | .02 |

[a]The 600 band never appeared without a 175 band.
[b]1 = select, 2 = choice⁻, 3 = choice°, 4 = choice⁺, 5 = prime
[c,d]Means within a row with different superscripts differ (P < .01).

As shown in Table 4, cattle whose DNA generated only the 175 base pair band provided beef that tended to have more marbling than cattle whose DNA did not generate either of the markers of marbling. Furthermore, cattle whose DNA generated both the 175 base pair band and the 600 base pair band provided beef that had significantly more marbling than cattle whose DNA generated only the 175 base pair band or whose DNA did not generate either the 175 base pair band or the 600 base pair band.

These results indicate that the present method is useful for assessing the beef marbling traits of live cattle. Moreover, these results indicate that the present method is capable of detecting small differences in the marbling characteristics of beef from live cattle.

Although the invention has been described with regard to a number of preferred embodiments, which constitute the best mode presently known to the inventors for carrying out this invention, it should be understood that various changes and modifications as would be obvious to one having the ordinary skill in this art may be made without departing from the scope of the invention which is defined by the claims which are appended hereto.

What is claimed is:

1. A method of identifying bovine animals or carcasses having markers of tenderness comprising:
   a) extracting DNA from a sample obtained from a bovine animal or carcass;
   b) amplifying said DNA by a polymerase chain reaction (PCR) to provide a pool of PCR products, wherein said PCR employs a CSTN primer of 10 nucleotides in length which comprises the sequence of SEQ ID NO:2; and
   c) assaying said pool for the presence or absence of an oligonucleotide selected from the group consisting of an oligonucleotide of approximately 350 base pairs, an oligonucleotide of approximately 625 base pairs, an oligonucleotide of approximately 675 base pairs, an oligonucleotide of approximately 1450 base pairs, and combinations thereof;
   wherein the presence of one or more of said oligonucleotides indicates that said animal or said carcass has one or more markers of tenderness.

2. The method of claim 1 wherein the PCR is conducted under low stringency conditions.

3. The method of claim 1 wherein the sample is a blood sample obtained from a live bovine animal.

4. The method of claim 1 wherein the sample is a semen sample obtained from a live bovine animal.

5. The method of claim 1 wherein the sample is a tissue sample obtained from a bovine animal carcass.

6. A method of identifying either bovine animals or carcasses having markers of marbling comprising:
   a) extracting DNA from a sample obtained from a bovine animal or carcass;
   b) amplifying said DNA by a polymerase chain reaction (PCR) to provide a pool of PCR products, wherein said PCR employs a CPN primer of 10 nucleotides in length which comprises the sequence of SEQ ID NO:4; and
   c) assaying said pool for the presence or absence of an oligonucleotide of approximately 175 base pairs, or an oligonucleotide of approximately 600 base pairs, or both of said oligonucleotides;
   wherein the presence of one or more of said oligonucleotides indicates that said animal or said carcass has one or more markers of marbling.

7. The method of claim 6 wherein the PCR is conducted under low stringency conditions.

8. The method of claim 6 wherein the sample is a blood sample obtained from a live bovine animal.

9. The method of claim 6 wherein the sample is a semen sample obtained from a live bovine animal.

10. The method of claim 6 wherein the sample is a tissue sample obtained from a bovine animal carcass.

11. A method of identifying bovine animals whose genome contains markers of tenderness and marbling, comprising:
    a) extracting DNA from a sample obtained from a bovine animal;
    b) amplifying a portion of said DNA by a first PCR to provide a first pool of PCR products, wherein said first PCR employs a CSTN primer said primer being 10 nucleotides in length and comprising the sequence of SEQ ID NO:2; and
    c) assaying said first pool for the presence or absence of an oligonucleotide selected from the group consisting of an oligonucleotide of approximately 350 base pairs, an oligonucleotide of approximately 625 base pairs, an oligonucleotide of approximately 675 base pairs, an oligonucleotide of approximately 1450 base pairs, and combinations thereof;
    wherein the presence of one or more of said oligonucleotides indicates that said animal or said carcass has one or more markers of tenderness;
    d) amplifying a portion of said DNA by a second PCR to provide a second pool of PCR products, wherein said second PCR employs a CPN primer, said primer being 10 nucleotides in length and comprising the sequence of SEQ ID NO:4; and
    e) assaying said second pool for the presence or absence of an oligonucleotide of approximately 175 base pairs, or an oligonucleotide of approximately 600 base pairs, or both of said oligonucleotides;
    wherein the presence of one or more of said oligonucleotides indicates that said animal or said carcass has one or more markers of marbling.

12. A primer for identifying bovine animal carcasses whose DNA comprises a marker of beef tenderness, said primer being 10 nucleotides in length and comprising the sequence of SEQ ID NO.2.

13. A primer for identifying bovine animal carcasses whose DNA comprises a marker of beef marbling, said primer being 10 nucleotides in length and comprising the sequence of SEQ ID NO.4.

14. A kit for identifying bovine animals whose DNA comprises one or more markers of beef marbling and one or more markers of beef tenderness, said kit comprising:
    (a) a container containing a CSTN primer, said CSTN primer being 10 nucleotides in length and comprising the sequence of SEQ. ID NO.2
    (b) a container containing a CPN primer, said CPN primer being 10 nucleotides in length and comprising the sequence of SEQ. ID NO.4.

15. The kit of claim 4 wherein said CSTN primer is 10 to 12 nucleotides in length and comprises the sequence of SEQ. ID NO:2; and
    wherein said CPN primer is 10 to 12 nucleotides in length and comprises the sequence of SEQ. ID NO:4.

16. The method of claim 1 wherein the sample is a blood sample obtained from a live heifer, steer, or bull.

17. The method of claim 1 wherein the sample is a semen sample obtained from a live bull.

18. The method of claim 6 wherein the sample is a blood sample obtained from a live heifer, steer, or bull.

19. The method of claim 6 wherein the sample is a semen sample obtained from a live bull.

* * * * *